United States Patent
Khoury et al.

(10) Patent No.: US 6,624,190 B2
(45) Date of Patent: Sep. 23, 2003

(54) 2-ACYLAMINO-2-DEOXY-GLUCONO-1,5-LACTONES, A METHOD FOR THE PRODUCTION THEREOF, COMPOSITIONS CONTAINING THEM, AND USES THEREOF

(75) Inventors: Chadi Khoury, Zahle (LB); Michel Minier, Antony (FR); Francois Le Goffic, Clamart (FR)

(73) Assignee: Universite Pierre et Marie Curie (Paris VI), Paris (FR)

( * ) Notice: Subject to any disclaimer, the term of this patent is extended or adjusted under 35 U.S.C. 154(b) by 0 days.

(21) Appl. No.: 09/859,997

(22) Filed: May 17, 2001

(65) Prior Publication Data

US 2002/0028954 A1 Mar. 7, 2002

Related U.S. Application Data

(63) Continuation of application No. PCT/FR99/02861, filed on Nov. 19, 1999.

(30) Foreign Application Priority Data

Nov. 19, 1998 (FR) .............................. 98 14564

(51) Int. Cl.$^7$ ................ A61K 31/351; A61K 7/00; C07D 309/10; C07D 309/14; C07C 15/107
(52) U.S. Cl. ................ 514/459; 514/460; 549/292; 549/293; 424/401; 585/455
(58) Field of Search ................ 549/292, 293; 514/459, 460; 585/455; 424/401

(56) References Cited

U.S. PATENT DOCUMENTS 5,505,938 A   4/1996   Pocalyko et al.
5,728,661 A   3/1998   Petit et al.

FOREIGN PATENT DOCUMENTS

EP   0 808 842 A2   11/1997

OTHER PUBLICATIONS

Wolk et al., "28. synthesis and enzyme–inhibition studies of phenylsemicarbazones dervied from $_D$–Glucono–1,5–lactone and 2–Acetamido–2–deoxy–$_D$–glucono–1,5–lactone," *Helvetica Acta*, vol. 75, pp. 323–334 (1992).

Knapp et al., "NAG–thiazoline, An N–Acetyl–θ–hexosaminidase inhibitor that implicates acetamido participation," *J. Am. Chem. Soc.*, vol. 118, pp. 6804–6805 (1996).

Kida et al., "New cleavable surfactants derived from Glucono–1,5–Lactone," *JAOCS*, vol. 71, No. 7, pp. 705–710 (Jul. 1994).

Kwoh et al., "Regioselective synthesis and characterization of 6–O–alkanoylgluconolactones," *Carbohydrate Research*, vol. 274, pp. 111–121 (1995).

Pokorny et al., "The inhibitory activity of 2–acetamido–2–deoxy–$_D$–gluconolactones and their isopropylidene derivatives on 2–acetamido–2–deoxy– θ–$_D$–glucosidase," *Carbohydrate Research*, vol. 37, pp. 321–329 (1974).

Panday et al., "Synthesis and evaluation of indolizine–type inhibitors of N–Acetyl–θ–$_D$–glucosaminidases," *Helvetica Chimica Acta*, vol. 81, pp. 475–490 (1998).

Kitagawa et al., "Chemical Transformation of Uronic Acids Leading to Aminocyclitols. II. Synthesis of Hexaacetyl–streptamine from N–Acetyl–D–Glucosamine", *Chemical and Pharmaceutical Bulletin*, vol. 26, No. 12, pp. 3825–3831, 1978.

Yoshikawa et al., "Chemical Transformation of Uronic Acids leading to Aminocycliols. IV. Synthesis of Hexaacetyl–streptamine from N–Acetyl–D–Glucosamine by means of Electrolytic Degradation", *Chemical and Pharmaceutical Bulletin*, vol. 29, No. 9, pp. 2582–2586, 1981.

2000, International Search Report for PCT/FR99/02861.

*Primary Examiner*—Taofiq Solola
(74) *Attorney, Agent, or Firm*—Merchant & Gould P.C.

(57) ABSTRACT

The invention concerns compounds of formula (I) wherein: A represents $R_1$ or $(O)R_1$ where $R_1$ represents an alkyl group comprising 1 to 30 carbon atoms, linear or branched, saturated or unsaturated, capable of being partly or totally substituted by Hal where Hal represents —Cl,—Br, or —F, and of being interrupted by one or several units selected among —O—,—S—,—C(O)—,—$NR_3$C(O)—, —Ph($R_4$)$_n$— and —$CH_2$—$CH_2$—O)$_{n'}$—, wherein $R_3$ represents or —($CH_2$)$_{n''}$—CH where n"=0 to 17; $R_4$ represents, —$CH_3$,—$CH_2H_5$,—$C_3H_7$ and n=0 to 4 and n'=1, 2, or 3, or $R_1$ represents a cyclanic radical with diterpene or triterpene root; and $R_2$ represents a $C_1$-$C_{11}$ linear or branched alkyl group. The invention also concerns a method for obtaining said compounds, compositions containing them and their use as surfactant, and in enzymatic processes using a chitinase, in particular N-acetylglucosaminidase.

16 Claims, 4 Drawing Sheets

2-ACYLAMINO-2-DEOXY-GLUCONO-1,5-LACTONES, A METHOD FOR THE PRODUCTION THEREOF, COMPOSITIONS CONTAINING THEM, AND USES THEREOF

This application is a continuation of international application No. PCT/FR99/02861, filed Nov. 19, 1999.

BACKGROUND OF THE INVENTION

1. Field of the Invention

The present invention relates to new substituted 2-acylamino-2-deoxy-glucono-1,5-lactone type compounds, to compositions containing said compounds that are surfactants and/or biologically active compounds, to methods for producing said compounds and to intermediates in their production.

2. Prior Art

Examples of glycosylated surfactants comprising a lactone function have been cited in the literature. Pocalyko et al., (1996) (5) and Kwoh et al. (1995) (3) describe the enzymatic synthesis of 6—O-dodecyl gluconolactone, while Kida et al. (1994) (1) use the lactone function to synthesise surfactants that are degradable in an acidic medium.

However, such lactones do not contain an N-acyl moiety or an N-acetylglucosamine moiety; this moiety is important in the recognition of certain enzymes.

Examples of the synthesis of N-acetyl glucosaminidase inhibitors have been cited in the literature by Pokorny et al., (1974) (6); Wolk et al. (1992) (7); Knapp et al. (1996) (2); and Panday et al. (1998) (4). These inhibitors exhibit major disadvantages; in particular, their low dissociation constant (between 0.13 and 0.45 $\mu$M) makes these potent inhibitors useless as regards affinity separation, as recovering the enzyme requires operating conditions that could cause them to denature. None of the molecules concerned has surfactant properties, in particular 2-acetamido-2-deoxy-glucono-1,5-lactone (Pokorny et al., 1974). As a result, their purely hydrophilic nature does not enable them to interact with biological membranes with a view to possible cellular penetration or disruption, or with amphiphilic compounds organised into micelles or liposomes with a view to vectorising or to liquid/liquid separation.

We have now developed a new class of substituted 2-acylamino-2-deoxy-glucono-1,5-lactone type compounds that may have the advantage of having surfactant or biodegradability properties and may be biologically active.

BRIEF SUMMARY OF THE INVENTION

The present invention provides compounds with formula (I):

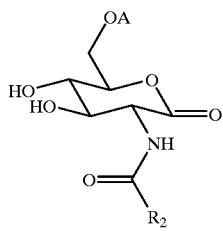

where A represents $R_1$ or —C(O)$R_1$, where $R_1$ represents a linear or branched, saturated or unsaturated alkyl group containing 1 to 30 carbon atoms, which may be partially or completely substituted by —Hal where Hal signifies —Cl, —Br, —I or —F, and which may be interrupted by one or more moieties selected from —O—, —S—, —C(O)—, —NR$_3$C(O)—, —Ph(R$_4$)$_{n\_}$—, and —CH$_2$—CH$_2$—O)$_{n'\_}$, where R$_3$ represents —H or —CH$_2$)$_{n''}$—CH$_3$ where n" is 0 to 17; R$_4$ represents —H, —CH$_3$, —C$_2$H$_5$, —C$_3$H$_7$ and n is 0 to 4 and n' is 1, 2 or 3, or R$_1$ represents a cyclane radical with a diterpene or triterpene root; and R$_2$ represents a linear or branched C$_1$ to C$_{11}$ alkyl group.

The compounds of the invention have the advantages of glycosylated glucosamine-based surfactants such as biodegradability.

Further, some of these compounds may have antimicrobial and antifungal properties. Finally, these compounds may be useful in enzymatic inhibition or enzyme recognition methods.

The invention al so concerns methods for preparing compounds with the above formula I. These methods comprise at least the following steps:

a) acylating glucosamine hydrochloride using an acid chloride with formula R$_2$C(O)Cl;

b) protecting the C1 hydroxyl group by a P$_1$ group, and the C3 and C4 hydroxyl group by groups P$_2$ and the C6 hydroxyl group;

c) deprotecting the protected C6 hydroxyl group;

d) 6—O-acylation with a compound with formula R$_1$C(O)Cl or 6—-alkylation with a compound with formula R$_1$Hal to obtain the compound with formula:

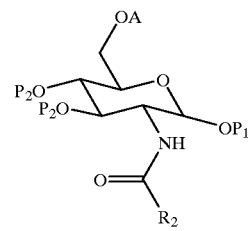

e) deprotecting the protected C1 hydroxyl group to obtain the compound with formula:

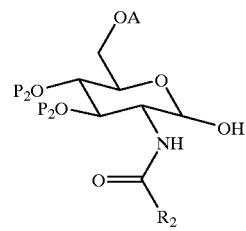

f) oxidising the compound obtained at e) to obtain the compound with formula:

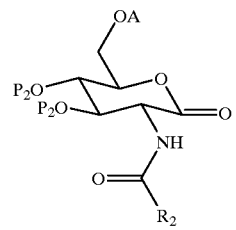

g) deprotecting the protected C3 and C4 hydroxyl groups of the compound obtained in f) to obtain the compound with formula I;

where A, $R_2$ and Hal have the same meanings as those given above, and $P_1$ and $P_2$ are protective groups.

In a further aspect, the invention concerns, as intermediate compounds, compounds with the following formulae:

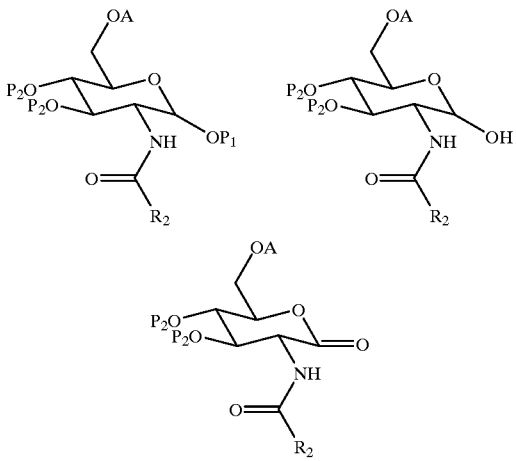

where A, $R_2$, $P_1$ and $P_2$ have the meanings given above.

Further, the present invention concerns compositions comprising at least one or more compounds of the invention, one or more compounds obtained by the method of the invention or intermediate products in said method.

Finally, the invention concerns compounds with formula I as surfacts or compounds for use in an enzymatic inhibition method or an enzyme recognition method.

The present invention will be better understood from detailed description and examples below and from the accompanying figures.

DETAILED DESCRIPTION OF THE PREFERRED EMBODIMENTS OF THE INVENTION

Figure 1:
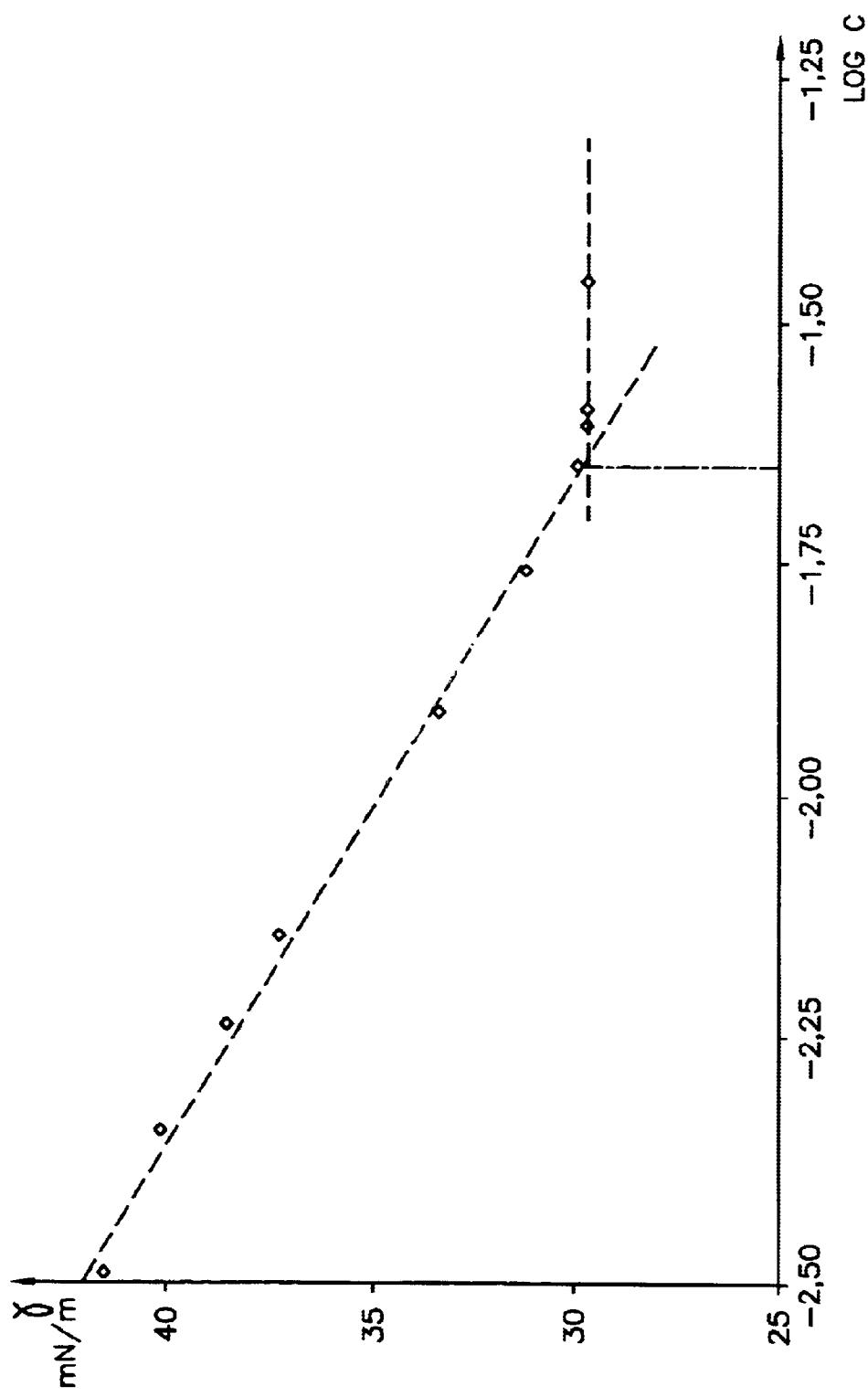
FIG. 1 shows the variation in the surface tension of water as a function of the logarithm of the concentration (in mol/l) of the compound of the invention with formula I, where A is $C(O)C_7H_{15}$ and $R_2$ is $CH_3$.

Preferred compounds of the invention are those where A is $C(O)R_1$ where $R_1$ represents a group containing 1 to 21 carbon atoms, preferably a linear $C_5$ to $C_{21}$ alkyl group.

Further preferred compounds of the invention are those wherein $R_2$ represents an n—$C_pH_{2p+1}$ alkyl group, where p is 1 to 7.

One preferred compound of the invention is that wherein A is $C(O)$-n-$C_7H_{15}$ and $R_2$ is $CH_3$.

In the preferred case of 2-acetamido-2-deoxy-6—O-octanoyl-glucono-1,5-lactone, specific recognition of N-acetyl glucosaminidase type enzymes has been demonstrated and quantified.

The importance and originality of this molecule resides in two major points: firstly, its surfactant nature, revealed by a reduction in the surface tension of water from 71 to 30 mN/m and by its critical micellar concentration of the order of 25 mM (Example 2). These data are comparable with those of commercially available glycosylated surfactants such as HECAMEG or n-octyl glucoside which are widely used in biochemistry, for example to dissolve membrane proteins, to form liposomes or to stabilise immunoenzymatic conjugates for ELISA. The relatively high CMC of this molecule (25 mM) renders it readily eliminatable by dialysis while its structure allows it to be assayed using HPLC.

The lactone structure of this molecule endows it with interesting biological properties such as specific recognition of N-acetyl glucosaminidases (Example 3). Compared with those of known inhibitors for this type of enzyme, its inhibition constant $K_1$ of the order of 3 $\mu M$ renders it suitable in an affinity separation context. The lactone (closed form) and gluconic acid (open form) equilibrium allows effective dissociation of the ligand/enzyme complex by changing the pH, for example.

The methods of the invention concern the preparation of a family of glycosylated surfactants from an N-acyl glucosamine.

Compounds with an N-acyl glucosamine structure are generally obtained from glucosamine hydrochloride produced by acid hydrolysis of chitin and an acid chloride. Thus in the preferred implementation of the method of the invention, the starting product is N-acetyl glucosamine (NAG).

For the protection steps, the above groups $P_1$ and $P_2$ are the usual protective groups suitable for the hydroxyl groups of carbohydrates. As an example, it is possible to use the allyl protective group for $P_1$ and the benzyl protective group for $P_2$, although other suitable protective groups should not be excluded.

Similarly, C6 protection can be carried out with a trityl (Tr) group although other suitable protective groups are not excluded: a hydroxyl group protected by Tr at C6 is deprotected in an acidic medium in this particular implementation.

Preferably, de-allylation is carried out under mild conditions; finally, in a particular implementation the C3 and C4 hydroxyl groups are deprotected by catalytic hydrogenation.

In the reaction scheme, Hal represents Cl, Br, I or F, chlorine and bromine being preferred in the implementation described below.

This synthesis method consists in:

1) protecting the C1 hydroxyl group using a $P_1$ group, for example allyl;
2) protecting the C6 hydroxyl group with a protective group, for example trityl (Tr);
3) protecting the C3 and C4 hydroxyl groups with $P_2$ groups, for example benzyl;
4) deprotecting the C6 hydroxyl group;
5) 6—O-acylating using an acid chloride or 6—O-alkylating using an alkyl halide;
6) C1 deprotection;
7) Oxidising at C1 to obtain the lactone; and
8) Deprotecting the C3 and C4 hydroxyl groups; using the following scheme:

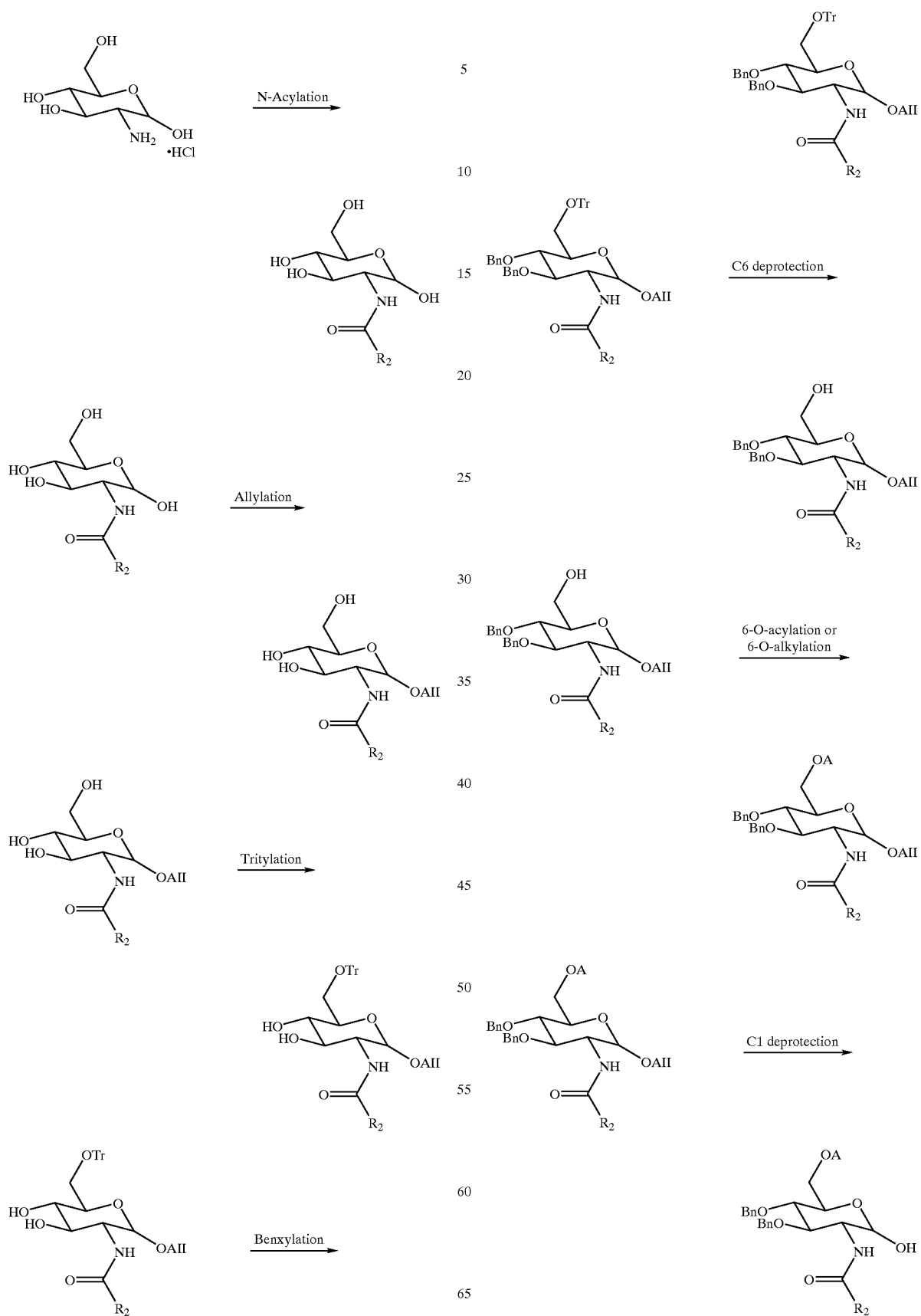

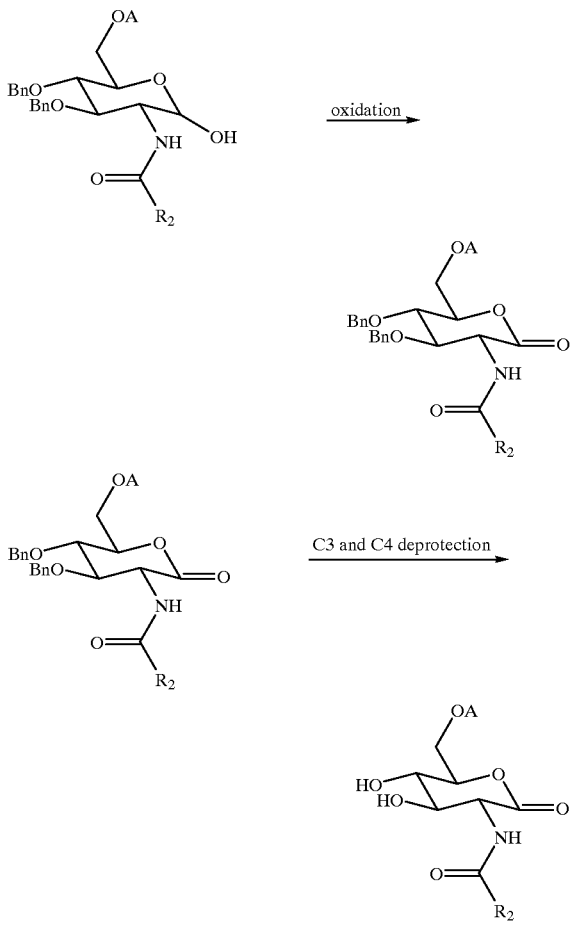

The structure and purity of the products obtained can be determined using mass spectrometry, by $^1$H and $^{13}$C NMR and by elemental analysis, as will be seen in the examples.

The surfactant properties of this particular example were determined by measuring the surface tension of solutions of different concentrations. The critical micellar concentration (CMC) was evaluated.

Further, the affinity of this molecule for different glycosidase type enzymes was estimated by studying inhibition of their activity. The test enzymes of the examples were bovine N-acetyl glucosaminidase, *S. marcescens* chitinases with a chitobiase activity, and lysozyme.

In a further aspect, the invention concerns compositions comprising the compounds of the invention. The above compounds can be used in the following applications and/or as a result of the following properties:

- as a surfactant ligand for liquid/liquid affinity separation;
- for their bactericidal or fungicidal effect resulting from inhibiting properties in association with facilitated cellular penetration;
- by inclusion in vesicles or liposomes for the transport of enzymes or active substances;
- for their possible incorporation in cosmetic or dermatological preparations;
- for their biological activity by enzyme inhibition, in particular enzymes from reactions involving N-acetylglucosamine, such as chitinases and N-acetyl glucosaminidases.

For this reason, the invention concerns compositions comprising at least one or more compounds of the invention, one or more compounds obtained by the method of the invention or one or more intermediate compounds.

These compositions can be provided for cosmetic or pharmaceutical use; they then comprise a support that is suitable for such applications. They can also be envisaged for a pesticidal, antibacterial, antifungal, insecticidal or antiviral application; they then comprise a support that is suitable for those applications.

The compositions of the invention can also be detergent compositions, for example intended for an industrial application.

The detergent compositions of the invention are characterized in that they contain 0.1% to 60% by weight of one or more compounds of the invention, also 40% to 99.9% of a support that is acceptable for this application, for example a detergent base. The detergent base is usually selected from anionic surfactants, non ionic, cationic or amphoteric surfactants and mixtures of such compounds.

The additive is usually selected from additives or mixtures of additives known in the detergent field.

The cosmetic compositions of the invention are characterized in that they contain 0.1% to 50%, preferably 5% to 35% by weight of one of more compounds of the invention and an excipient and/or a detergent base and/or additive.

The cosmetic compositions can be in the form of a soft liquid soap, shampoo, foam bath, shower gel or care formula, in particular a pommade, cream or milk, an aqueous solution or a hydroalcoholic solution.

When the composition of the invention is a soft liquid soap, it may contain 5% to 35% by weight of a compound of the invention and 70% to 95% by weight of an excipient.

Certain excipients, detergent bases and additives are generally selected from compounds that are well known to the skilled person. In particular, the compounds described in EP-A-0 769 499 may be cited.

When used to treat the skin or hair, they can be in the form of a cream, milk, emulsion (water-in-oil or oil-in-water), gel, or an aqueous or hydroalcoholic composition. They also contain additives such as fragrances, colorants, preservatives, thickening agents and emulsifiers, or any other usual product that is known in the art and routinely used to formulate compositions of that type.

Compositions intended to clean the hair can be in the form of an aqueous or hydroalcoholic solution, emulsion, cream, milk, gel and may be packaged as an aerosol with a propellant.

When the compositions are intended for pharmaceutical use, they comprise a pharmaceutically acceptable support and can be in the form of an aqueous solution, a hydroalcoholic solution, a gel, cream, syrup or aerosol and contain the usual additives that are pharmaceutically suitable for the intended use.

Formulations when the compounds of the invention are in the form of reverse micelles may be useful for their application to liquid—liquid extraction of N-acetyl glucosaminidase in particular. It is possible to envisage the preparation of solutions in an apolar solvent such as iso-octane for example, and comprising 50 to 250 mM of AOT (sodium dioctyl sulphosuccinate), 1 to 2.5 mM of one or more compounds of the invention, and 0.5 to 6 M of water, optionally with an added salt, and optionally comprising a buffer, for example (90% 0.1 M KCl/10% 0.01 M phosphate buffer, pH 7), and optionally one or more co-solvents and/or co-surfactants.

For some applications, it is possible to prepare unilamellar liposomes comprising, for example, phospholipids and one or more compounds of the invention in an aqueous medium.

Further, the compositions of the invention can be used for reasons of the biological properties of the compounds of the invention, in particular in a method for enzymatic inhibition or for enzyme recognition. The following examples include such compositions. In general, in addition to one or more compounds of the invention, they generally comprise water, an aqueous buffer, for example an acetate buffer, pH 4.5 (0.2 M) or a phosphate buffer, pH 6.6 (0.2 M); a hydroalcoholic support comprising one or more alcohols and the usual additives that are suitable for the given application.

The compositions can also be in the form of emulsions or pre-emulsions comprising, for example, the usual emulsifiers, additives and thickeners that are suitable for the desired application, or they can be in the form of a gel.

METHOD AND APPARATUS

Determination of Critical Micellar Concentration

The surface tension γ of a liquid in contact with air was measured at 25° C. by the Wilhelmy plate method (Prolabo TENSIMAT n3 tensometer). This consisted of plunging a vertical platinum strip (19.54 mm long) into a liquid then gradually withdrawing it, monitoring the tension exerted on the strip by the liquid film. The maximum value recorded before complete detachment of the strip represented the surface tension, expressed in mN/m. After calibrating the apparatus (calibration at two points: the zero value with the strip in air and a value of 50.2 mN/m with the strip tested with a weight of 200 mg), the surface tensions of solutions containing increasing quantities of the surfactant were recorded (measurements repeated three times). The critical micellar concentration was obtained from conventional graphs of γ=f(logC) where C represents the concentration in mol/l.

Enzymatic Inhibition Study a) N-acetyl glucosaminidase (NaGase)

The enzyme used as a reference was bovine kidney β—N-acetyl glucosaminidase (EC 3.2.1.52) (Sigma A-2415) and its substrate was p-nitrophenyl 2-acetamido-2-deoxy glucopyranoside (Acros 22941–1000) (pNphNAG). The commercially available enzyme, in the form of a suspension in a 3.2 M solution of $(NH_4)_2SO_4$, was centrifuged at 13000 rpm for 5 minutes and the residue was taken up in 1 ml of water. The solution obtained was the mother enzymatic solution.

Protocol: 100 μl of the enzymatic solution diluted to 1/10 was mixed with 100 μl of pH 4.2 citrate buffer and 300 μl of inhibitor solution (or water for the reference) and incubated at 37° C. for 5 minutes in a spectrophotometer cell. After adding 500 μl of substrate (5 mM or 2.5 mM), incubation was continued for 8 minutes at 37° C. and the optical density at 400 nm was monitored. The quantity of p-nitrophenol liberated by the enzymatic reaction was determined by correlating the optical density to a calibration curve (OD at 400 nm=f([p-nitrophenol])). The N-acetyl glucosaminidase activity unit was defined as the quantity of enzyme required to liberate one μmole of p-nitrophenol per minute under the conditions cited above.

b) *Serratia marcescens* chitinases

In this case, the chitobiase activity of a solution of chitinases partially purified on a Mono P 5/20 anion exchange column (Pharmacia) was studied. The substrate used was 5 mM pNphNAG.

Protocol: 100 μl of the enzymatic solution, diluted 4-fold, was mixed with 100 μl of pH 4.2 citrate buffer and 300 μl of inhibitor solution (or water for the reference) in a spectrophotomoter cell. After incubating for 5 minutes at 37° C., 500 μl of 5 mM pNphNAG solution was added. The kinetics of the optical density change at 400 nm were monitored for 8 minutes. The quantities of p-nitrophenol liberated were compared for samples containing increasing quantities of inhibitor.

c) Lysozyme

The enzyme studied was 0.5 g/l chicken lysozyme (Sigma, L-6876) in a 100 mM, pH 6.5 phosphate buffer and the substrate was constituted by 17 mg/100 ml of *Micrococcus lysodeikticus* walls in suspension in the same buffer.

Protocol: 100 μl of enzymatic solution was diluted with 400 μl of inhibitor solution. This was left at ambient temperature for 5 or 10 minutes. 40 μl of mixture was added to 3 ml of the substrate suspension in a spectrophotometer cell. The optical density was recorded at 450 nm every 10 seconds for 3 minutes.

$I_{50}$ is defined as the concentration of compound capable of inhibiting 50% of the enzymatic activity under the assay conditions.

EXAMPLE 1

Chemical synthesis of 2-acetamido-2-deoxy-6—O-octanoyl-glucono-1,5 lactone from N-acetyl glucosamine (NAG)

Step 1) consisted of preparing allyl 2-acetamido-2-deoxy-glucopyranoside (b) from NAG 35 g of NAG and 3.5 ml of $BF_3,Et_2O$ were added to 350 ml of allyl alcohol under argon then heated under reflux for 3 hours. After cooling, the solvents were evaporated off to produce a pale yellow colored solid gel. This was washed overnight in ether then recovered by filtering. After grinding and drying the aggregates, a white powder was obtained: 40 g (yield 97%).

Step 2 consisted of preparing allyl 2-acetamido-2-deoxy-6—O-trityl-glucopyranoside (c)

8.4 g of (b) was added to 90 ml of pyridine containing 12 g of triphenylmethane chloride (TrCl). After reacting at ambient temperature for 24 hours, the reaction mixture was heated to 90° C. for 1 h. after cooling, the mixture was poured into ice water then extracted with chloroform. After washing with water, drying, then evaporating off the solvents, a thick gum was obtained. This latter was taken up in absolute ethanol then re-precipitated from ether to produce a brown solid: 10.5 g (yield: 65%).

Step 3 consisted of preparing allyl 2-acetamido-2-deoxy-6—O-trityl-3,4—O-dibenzyl-glucopyranoside (d)

10 g of (c), 12 g of KOH and 7 ml of benzyl bromide in 340 ml of toluene were heated under reflux for 3 h. The suspension obtained was then hot filtered through Celite and the solid residues were washed with hot toluene. The filtrates were then combined and washed. After washing and evaporating off the solvents, a yellow-white solid was obtained: 12 g (yield: 88%).

Step 4 consisted of preparing allyl 2-acetamido-2-deoxy-3,4—O-dibenzyl-glucopyranoside (e)

5 g of (d) was dissolved in 125 ml of a methanol/dichloromethane mixture (30:70) containing 4% (m/v) of para-toluene sulphonic acid (PTSA). This was stirred at ambient temperature for 3 h. The reaction mixture was then neutralised, washed with water and dried. After evaporating off the solvents, the crude product obtained was purified over silica to produce a white solid: 2 g (yield: 62%).

Step 5 consisted of preparing allyl 2-acetamido-2-deoxy-6—O-octanoyl-3,4—O-dibenzyl-glucopyranoside (f)

9.5 g of (e) and 5 g of octanoyl chloride in 150 ml of toluene was heated under reflux at 90–95° C. for 4 h. After cooling, the reaction mixture was poured into 600 ml of water and extracted with toluene. The organic phases were combined, washed with $NaHCO_3$ then with water. Finally, after drying and evaporating off the solvents, the crude product was purified over silica to recover 8.6 g of (f) (Yield: 70%).

Step 6 consisted of preparing allyl 2-acetamido-2-deoxy-6—O-octanoyl-3,4—O-dibenzyl-glucopyranose (g)

8 g of (f), 1.2 g of diazabicyclooctane (DABCO) and 3 g of tris triphenylphosphine rhodium chloride ($Rh(PPh_3)_3Cl$) in 400 ml of an aqueous methanol solution (90% v/v) were heated under reflux for 4 hours. After filtering through paper and concentrating, it was taken up in 250 ml of chloroform, washed with 5% (m/v) citric acid then with water. After drying and evaporating off the solvents, the crude mixture was taken up in 150 ml of an aqueous acetone solution (90%, m/v). 3 g of $HgCl_2$ was added and it was stirred at ambient temperature for 60 minutes.

The solvents were then evaporated off and the residues were taken up in chloroform. The organic phase was washed with a saturated KI solution then with water. After drying, evaporating off the solvents provided a thick oil. Silica column chromatography produced the pure product: 5 g (yield: 67%).

Step 7 consisted of preparing 2-acetamido-2-deoxy-6–0-octanoyl-3,4—O-dibenzyl-glucono-1,5-lactone (h)

5 ml of dichloromethane (DCM) containing 0.16 ml of oxalyl chloride was cooled to −70° C. in a three-necked flask provided with a dropping funnel and an argon inlet/outlet. 0.26 ml of dimethylsulphoxide diluted in 4 ml of DCM was added dropwise and the mixture was left at −70° C. with stirring for 10 minutes. 200 mg of (g) was dissolved in DCM then added to the mixture dropwise. After reacting for 45 minutes, 1 ml of triethylamine (TEA) was added and it was kept at −70° C. for 30 minutes. The mixture was brought to ambient temperature and washed with water. The two phases were separated and the aqueous phase was extracted twice with DCM. The organic phases were combined and washed with a 1 N HCl solution, a 5% $NaHCO_3$ solution then three times with water. The concentration of the organic phase produced a clear oil in an amount of 187 mg. Yield: 94%.

Step 8 consisted of preparing 2-acetamido-2-deoxy-6—O-octanoyl-glucono-1,5-lactone (i)

160 mg of (h) was dissolved in 10 ml of methanol containing 180 mg of palladium on charcoal, 10%. The suspension was stirred in hydrogen overnight. The catalyst was removed by filtering through filter paper and the filtrate was filtered again through cotton. Evaporating off the solvent provided 92 mg of a solid gel (yield: 87%).

Empirical formula $C_{16}H_{27}NO_7$. Molar mass: 345.

Mass spectrometry:

$[M+H]^+346$ $[M+NH_4]^+=363$ $^1H$ NMR (solvent: deuterated DMSO):

δ(ppm)=0.82 (t, 3H, $CH_3$); 1.21 (m, 8H, $CH_2$); 1.48 (m, 2H, $CH_2$); 1.89 (s,3H, $CH_3$); 2.29 (t, 2H, $CH_2$); 3.2–4.87 (m, 8H, OH, CH, $CH_2$); 7.99 (d, 1H, NH).

$^{13}C$ NMR (solvent: deuterated DMSO):

δ(ppm)=14.0; 22.1; 22.5; 24.5; 28.5; 28.5; 31.2; 33.6; 55.8; 65.9; 68.5; 69.3; 71.6; 169.6; 171.4; 173.1.

Elemental analysis:

| | Calculated | | Found |
|---|---|---|---|
| C: | 55.6% | C: | 51.8% |
| H: | 7.82% | H: | 7.72% |
| N: | 4.05% | N: | 4.08% |

EXAMPLE 2

Surfactant Properties. Determination of Critical Micellar Concentration (CMC)

The change in surface tension γ (in mN/m) of an aqueous solution (volume=10 ml) was monitored as a function of the quantities of dissolved product (C, in Mol/l) ($A=C(O)C_7H_{15}$ and $R_2=CH_3$). The results obtained are shown in FIG. 1. The critical micellar concentration corresponds to the concentration above which the surface tension becomes a constant.

Note firstly the surfactant nature of the molecule, confirmed by the reduction in surface tension from 71 to 30 mN/m for concentrations of 0 to 25 mM (i.e., 8.6 g/l).

The CMC of 2-acetamido-2-deoxy-6—O-octanoyl glucono-1,5-lactone was 25 mM, and was of the same order of magnitude as that of HECAMEG (22 mM) and octyl glucoside (18 mM).

EXAMPLE 3

Biological Properties: Enzymatic Inhibition

The affinity of 2-acetamido-2-deoxy-6—O-octanoyl glucono-1,5-lactone from Example 2 for 3 types of glycosidases, bovine N-acetyl glucosaminidase, *Serratia marcescens* chitinases and chicken lysozyme, was tested by evaluating the inhibiting power of this molecule on those enzymes.

a) Bovine N-acetyl glucosaminidase

Figure 2:
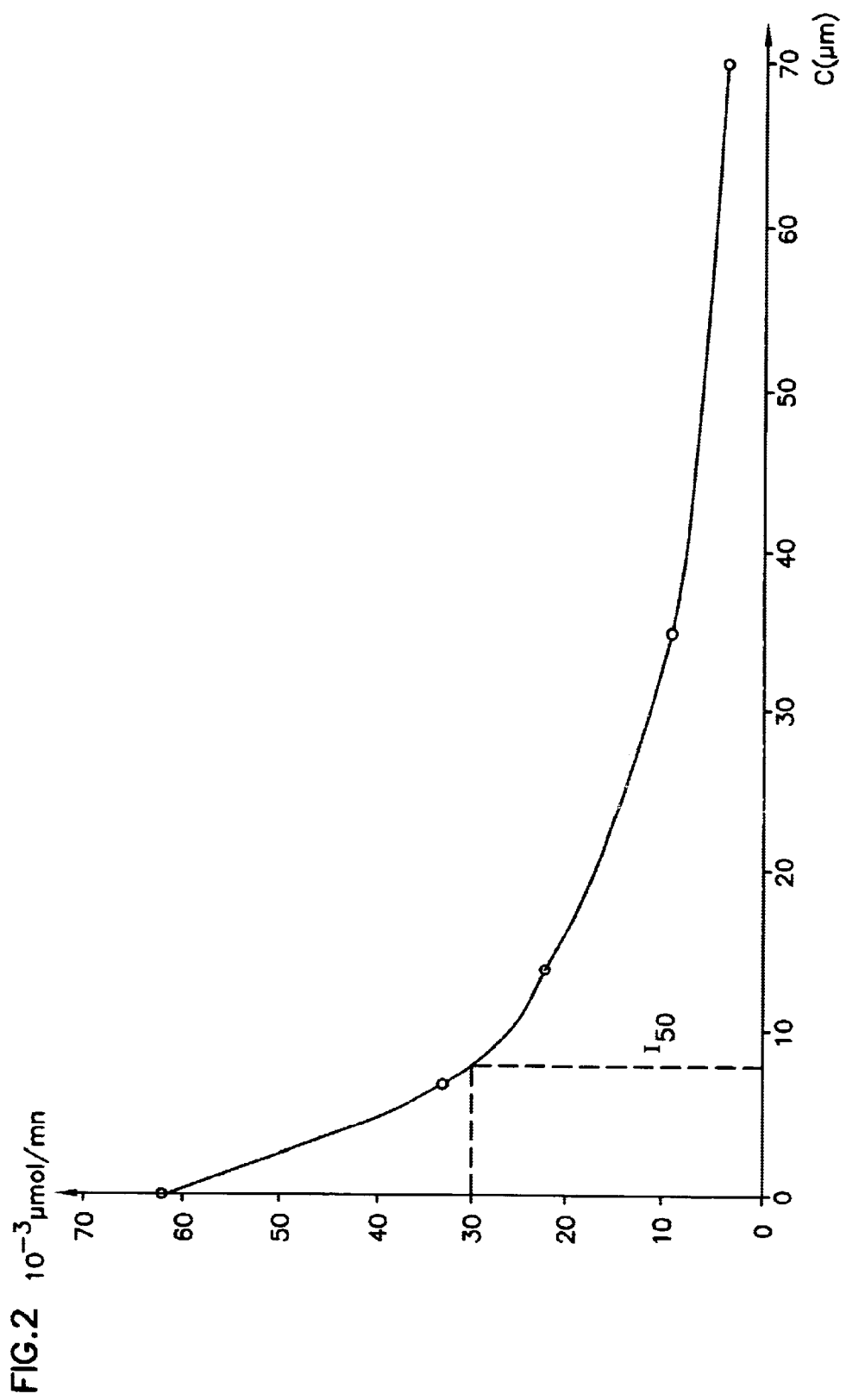
FIG. 2 illustrates the inhibiting effect of 2-acetamido-2-deoxy-6—O-octanoyl-glucono-1,5-lactone with formula I, where A is $C(O)C_7H_{15}$ and $R_2$ is $CH_3$, on bovine N-acetyl glucosaminidase.

We colorimetrically monitored the quantities of p-nitrophenol liberated (in $10^{-3}$ μmol/mn) by the action of N-acetyl glucosaminidase (NaGase) on pNphNAG (2.5 mM) in the presence of increasing quantities of (i) (concentration C in mM). The results illustrating the NaGase activity obtained are shown in FIG. 2.

Inhibition of N-acetyl glucosaminidase by (i) had thus been demonstrated. The $I_{50}$ of (i) is of the order of 7 μM.

In order to determine the inhibition constant $K_1$, we used Dixon's graphical method, which consisted of plotting the inverse of the initial velocity (1 Iv0) of the enzymatic reaction against the inhibitor concentration (C, in μM) for two different substrate concentrations. The abscissa of the intersection point of the two straight lines corresponds to $—K_1$.

Figure 3:
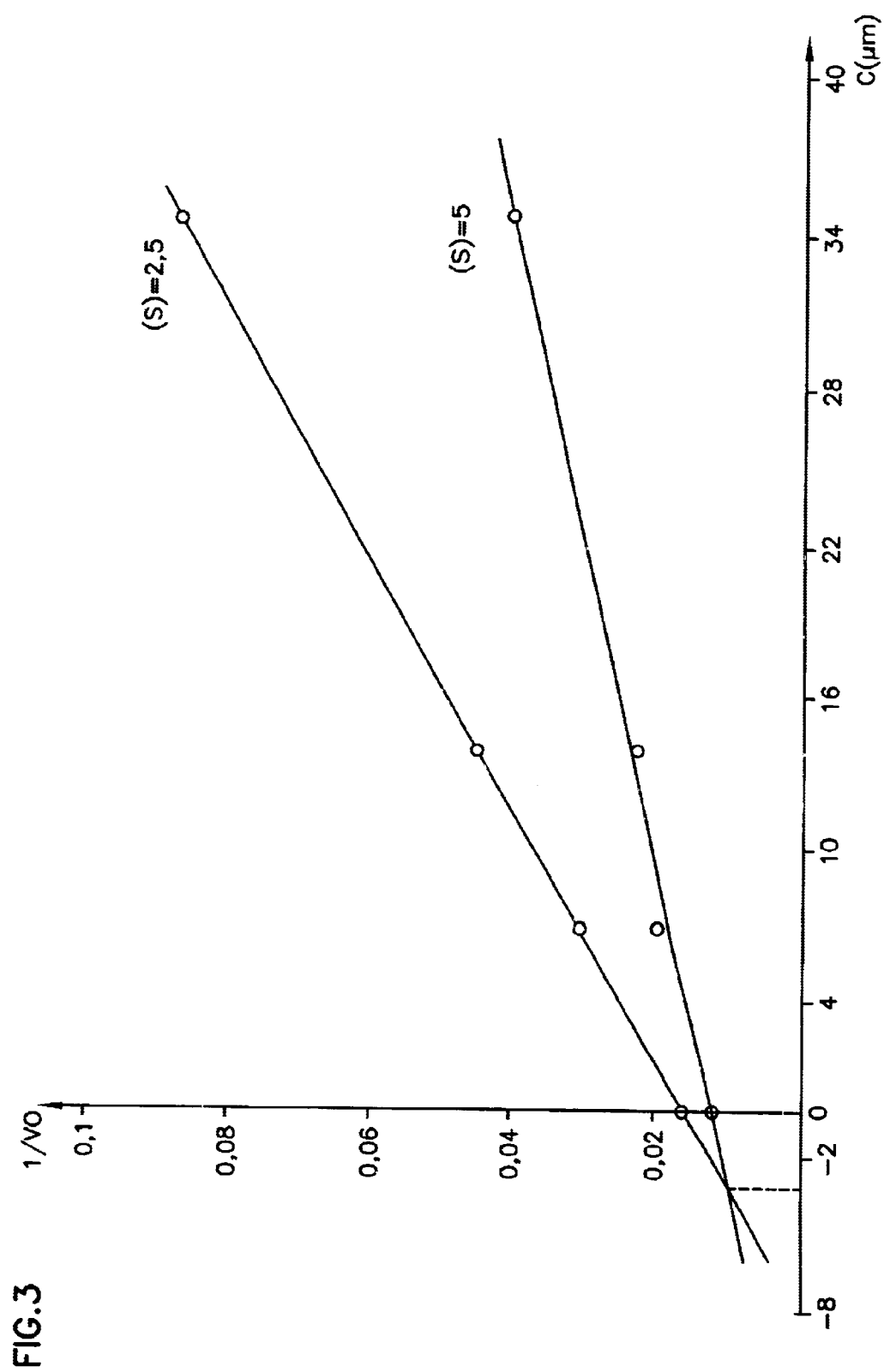
FIG. 3 shows a Dixon diagram confirming competitive inhibition of N-acetyl glucosaminidase by the compound of the invention with formula I where A is $C(O)C_7H_{15}$ and $R_2$ is $CH_3$.

With the two concentrations of substrate, 2.5 mM and 5 mM, we obtained the straight lines shown in FIG. 3. These results confirm the competitive inhibiting nature of (i), shown by analogues of the transition state, and provided an estimate for $K_1$ of the order of 3 µM.

b) *Serratia marcescens* chitinases

In the same manner, the quantities of p-nitrophenol liberated by the chitobiase activity of *S. marcescens* chitinase-son p-nitrophenyl-NAG in the presence of concentrations (C, in µM) of (i) of 0 to 1. mM were measured.

Figure 4:
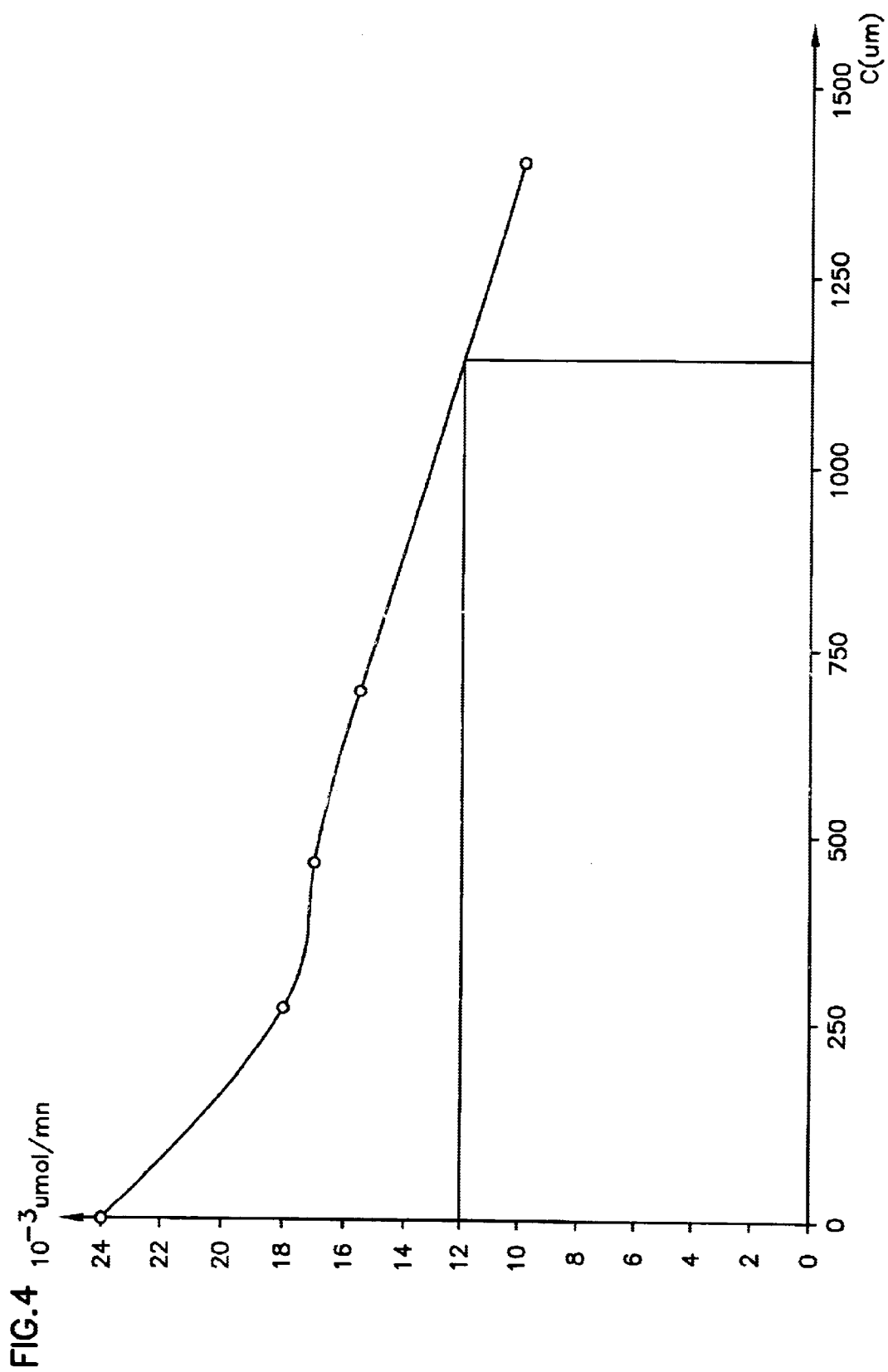
FIG. 4 illustrates the inhibiting effect of the compound wherein A is $C(O)C_7H_{15}$ and $R_2$ is $CH_3$ on *Serratia marcescens* chitinases.

The results shown in FIG. 4 show that-acetamido-2-deoxy-6—O-octanoyl-glucono-1,5-lactone has an affinity for certain *Serratia marcescens* chitinases since this molecule inhibits the chitobiase activity of a partially purified sample of those enzymes.

In this case, the $I_{50}$ was of the order of 1.2 mM.

c) Lysozyme

No difference was detected between the activity of a 0.1 mg/ml lysozyme solution in the presence or otherwise of (i) in a concentration of 1.8 mM.

In summary, it can be concluded that 2-acetamido-2-deoxy-6—O-octanoyl-glucono-1,5-lactone (i) has more affinity for bovine N-acetyl glucosaminidase than for *S. marcescens* chitinases, and has no affinity for lysozyme.

REFERENCES (1) Kida T., Morishima N., Masuyama A. and Nakatsuji N. (1994): New cleavable surfactants derived from glucono-1,5-lactone. J. Am. Oil Chem. Soc. 71, (7), 705–710.
(2) Knapp S., Vocadlo D., Gao Z., Kirk B., Lou J. and Withers S. (1996): NAG-thiazoline, an N-acetyl-b-hexosaminidase inhibitor that implicates acetamido participation. J. Am. Chem. Soc. 118, 6804–6805.
(3) Kwoh D., Pocalyko D., Carchi A., Harirchian B., Hargiss L. and Wong T. (1995): Regioselective synthesis and characterization of 6—O-alkanoylgluconolactones. Carb. Res. 274, 111–121.
(4) Panday N., Granier T. and Vasella A. (1998): Synthesis and evaluation of indolizine-type inhibitors of N-acetyl-b-D-glucosaminidases. Helv. Chim. Acta 81, 475490.
(5) Pocalyko D., Carchi A., Harirchian B. and Vermeer R. (1996): Straight chain saturated C8–C18 alkyl aldonolactone esters and an enzymic method for their preparation. U.S. Pat. No. 5,505,938.
(6) Pokorny M., Zissis E., Fletcher H. G. and Pravdic N., (1974): The inhibitory activity of 2-acetamido-2-deoxy-D-gluconolactones and their isopropylidene derivatives on 2-acetamido-2-deoxy-b–D-glucosidase. Carb. Res. 37, 321–329.
(7) Wolk D., Vasella A., Schweikart F. and Peter M. (1992): Synthesis and enzyme-inhibition studies of phenylsemicarbazones derived from D-glucono-1,5-lactone and 2-acetamido-2-deoxy-D-glucono-1,5-lactone. Helv. Chim. Acta 75, 323–334.

What is claimed is:
1. A compound comprising the following formula I:

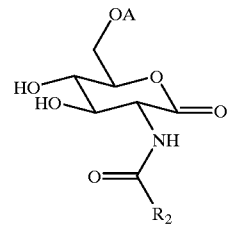

where A represents $R_1$ or —C(O)$R_1$, where $R_1$ represents a linear or a branched, a saturated or an unsaturated alkyl group containing 1 to 30 carbon atoms, which is partially or completely substituted by —Hal where Hal is —Cl, —Br, —I or —F, and which is interrupted by one or more moieties selected from —O—, —S—, —C(O)—, —NR$_3$C(O)—Ph (R$_4$)$_n$— and —(CH$_2$—CH$_2$—O)$_n$—, where $R_3$ represents —H or —(CH$_2$)$_n$"—CH$_3$, where n" is 0 to 17; $R_4$ represents —H, —CH$_3$, —CH$_5$ or —C$_3$H$_7$, n is 0 to 4 and n' is 1, 2 or 3; and $R_2$ represents a linear or a branched $C_1$ to $C_{11}$ alkyl group.

2. The compound according to claim 1, wherein A is a C(O)$R_1$ and wherein $R_1$ represents a group containing 1 to 21 carbon atoms.

3. The compound according to claim 1, wherein A is a linear $C_5$ to $C_{21}$ alkyl group.

4. The compound according to claim 1, wherein $R_2$ represents a n—$C_pH_{2p+1}$ alkyl group where p is 1 to 7.

5. The compound according to claim 1, wherein A is a C(O)—n—$C_7H_{15}$ and $R_2$ is a CH$_3$.

6. A method for preparing a compound of formula I:

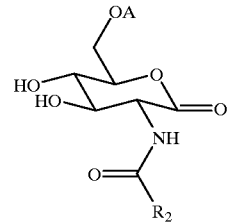

where A represents $R_1$ or —C(O)$R_1$, where $R_1$ represents a linear or a branched, a saturated or an unsaturated alkyl group containing 1 to 30 carbon atoms, which is partially or completely substituted by —Hal where Hal is —Cl, —Br, —I or —F, and which is interrupted by one or more moieties selected from —O—, —S—, —C(O)—, —NR$_3$C(O)— Ph(R$_4$)$_n$ — and —(CH$_2$—CH$_2$—O)$_n$ —, where $R_3$ represents —H or —(CH$_2$)$_n$ —CH$_3$ where n" is 0 to 17; $R_4$ represents —H, —CH$_3$, —C$_2$H$_5$ or —C$_3$H$_7$, n is 0 to 4 and n' is 1, 2 or 3; and $R_2$ represents a linear or branched $C_1$ to $C_{11}$ alkyl group; said method comprising the steps of:

a) acylating glucosamine hydrochloride using an acid chloride of formula $R_2$C(O)Cl;
b) protecting the C1, C3, C4 and C6 hydroxyl groups;
c) deprotecting the protected C6 hydroxyl group;
d) 6-O-acylating with a compound of formula $R_1$C(O)Cl or 6-O-alkylating with a compound of formula $R_1$Hal to obtain a compound of formula:

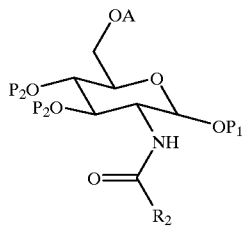

e) deprotecting the protected C1 hydroxyl group to obtain a compound with formula:

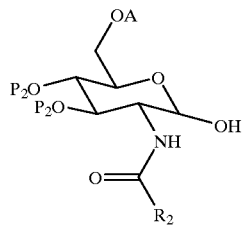

f) oxidizing the compound obtained at e) to obtain a compound with formula:

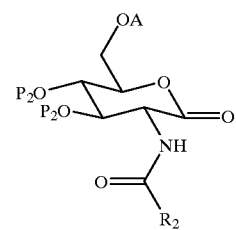

g) deprotecting the protected C3 and C4 hydroxyl groups of the compound obtained in f) to obtain the compound of formula I;

where Hal represents Cl, Br, I or F and $P_1$ and $P_2$ represent protecting groups.

7. A composition comprising at least one compound according to claim 1.

8. A composition comprising at least one compound obtained by the method of claim 6.

9. A surfactant composition comprising an amount of at least one compound according to claim 1, wherein said amount is effective as a surfactant and at least one support acceptable for said surfactant composition.

10. An enzymatic inhibiting composition comprising an amount of at least one compound according to claim 1, wherein said amount is effective to inhibit at least one enzyme.

11. A cosmetic composition comprising 0.1% to 50% by weight of at least one compound according to claim 1, at least one cosmetically acceptable support.

12. A detergent composition comprising at least one compound according to claim 1, and at least one support acceptable for said detergent composition.

13. A pharmaceutical composition comprising a pharmaceutically acceptable amount of at least one compound according to claim 1, and at least one support acceptable for said pharmaceutical composition.

14. A compound having the following formula I:

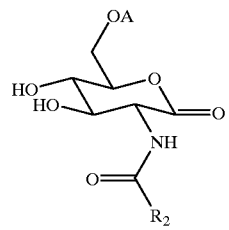

where A represents $R_1$ or —C(O)$R_1$, where $R_1$ represents a linear or a branched, a saturated or an unsaturated alkyl group containing 1 to 30 carbon atoms, which is partially or completely substituted by —Hal where Hal is —Cl, —Br, —I or —F, and which is interrupted by one or more moieties selected from —O—, —S—, —C(O)—, —NR$_3$C(O)—, —Ph(R$_4$)$_n$— and —(CH$_2$—CH$_2$—O)$_{n'}$—, where $R_3$ represents —H or —(CH$_2$)$_{n''}$—CH$_3$, where n' is 0 to 17; $R_4$ represents —H, —CH$_3$, —C$_2$H$_5$ or —C$_3$H$_7$, n is 0 to 4 and n' is 1, 2 or 3, or represents a cyclane radical with a diterpene root or a triterpene root; and $R_2$ represents a linear or a branched $C_1$ to $C_{11}$ alkyl group.

15. A method for preparing a compound of formula I:

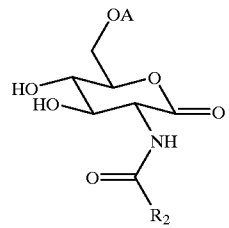

where A represents $R_1$ or —C(O)$R_1$, where $R_1$ represents a linear or a branched, a saturated or an unsaturated alkyl group containing 1 to 30 carbon atoms, which is partially or completely substituted by —Hal where Hal is —Cl, —Br, —I or —F, and which is interrupted by one or more moieties selected from —O—, —S—, —C(O)—, —NR$_3$C(O)—, —Ph(R$_4$)$_n$— and —(CH$_2$—CH$_2$—O)$_{n'}$—, where $R_3$ represents —H or—(CH$_2$)$_{n''}$—CH$_3$ where n" is 0 to 17; $R_4$ represents —H, —CH$_3$, —C$_2$H$_5$ or a —C$_3$H$_7$, n is 0 to 4 and n' is 1, 2 or 3, or $R_1$ represents a cyclane radical with a diterpene root or triterpene root; and $R_2$ represents a linear or branched $C_1$ to $C_{11}$ alkyl group;

said method comprising the steps of:

a) acylating glucosamine hydrochloride using an acid chloride of formula $R_2$C(O)Cl;

b) protecting the C1, C3, C4 and C6 hydroxyl group;

c) deprotecting the protected C6 hydroxyl group;

d) 6-O-acylating with a compound of formula $R_1$C(O)Cl or 6-O-alkylating of a compound with formula $R_1$Hal to obtain the compound of formula:

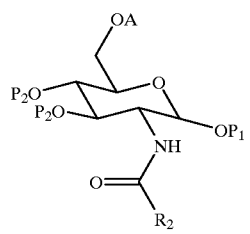

e) deprotecting the protected C1 hydroxyl group to obtain the compound of formula:

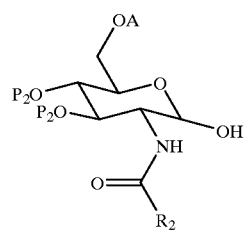

f) oxidizing the compound obtained at e) to obtain the compound of formula:

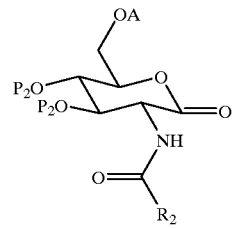

g) deprotecting the protected C3 and C4 hydroxyl groups of the compound obtained in f) to obtain the compound of formula I; where Hal represents Cl, Br, I or F and $P_1$ and $P_2$ represent protective groups.

16. A composition comprising at least one compound according to claim 14.

* * * * *